United States Patent [19]
Petrus

[11] Patent Number: 6,093,417
[45] Date of Patent: Jul. 25, 2000

[54] COMPOSITION TO TREAT EAR DISORDERS

[75] Inventor: Edward J. Petrus, Austin, Tex.

[73] Assignee: Advanced Medical Instruments, Austin, Tex.

[21] Appl. No.: 09/228,119

[22] Filed: Jan. 11, 1999

[51] Int. Cl.[7] .......................... A61K 31/495; A61K 31/56
[52] U.S. Cl. .......................... 424/437; 514/171; 514/254
[58] Field of Search .......................... 424/437; 514/171, 514/254

[56] References Cited

U.S. PATENT DOCUMENTS

| | | | |
|---|---|---|---|
| 3,946,123 | 3/1976 | Hanna | 426/643 |
| 4,025,620 | 5/1977 | Beyer et al. | 424/405 |
| 4,628,063 | 12/1986 | Haines et al. | 514/626 |
| 4,851,442 | 7/1989 | Watson | 514/553 |
| 4,914,131 | 4/1990 | Haines et al. | 514/626 |
| 4,933,184 | 6/1990 | Tsuk | 424/449 |
| 4,954,486 | 9/1990 | Guth | 514/158 |
| 4,956,391 | 9/1990 | Sapse | 514/810 |
| 5,061,729 | 10/1991 | Kineses et al. | 514/562 |
| 5,064,858 | 11/1991 | Sapse | 514/536 |
| 5,229,130 | 7/1993 | Sharma et al. | 424/449 |
| 5,238,933 | 8/1993 | Catz et al. | 514/236.2 |
| 5,447,930 | 9/1995 | Mayak | 514/239.2 |
| 5,462,749 | 10/1995 | Rencher | 424/484 |
| 5,827,529 | 10/1998 | Ono et al. | 424/448 |
| 5,837,289 | 11/1998 | Grasela et al. | 424/484 |
| 5,843,930 | 12/1998 | Purwar et al. | 514/171 |

OTHER PUBLICATIONS

Gabor et al., *Chemical Abstracts*, vol. 117, #163362, 1993.
Sakamoto, *World Patents Index*, vol. 78, #84512, 1978.
Van Lengerich et al., *Chemical Abstracts*, vol. 129, #8597, May 1998.
Shambaugm GE Jr, Zinc: The Neglected Nutrient *Am J Otol* 1989 Mar; 10(2):156–60.
Steel KP, A New Era in the Genetics of Deafness *Lancet* 1998;339:1545–47.
Prasher D, New Strategies for Prevention and Treatment of Noise–Induced Hearing Loss *Lancet* Oct. 17, 1998 p 1240 (1).
Thomas DW, An Earful of Auditory Advice *Dogworld* Nov. 1996; 38–9.
Townsend GC, Scheld WM, Adjunctive Corticosteroids for Adult Bacterial Meningitis *Infect Med* 1995; 12 (12);701–10.

Windler JA, Nasal Polyposis: Rationale for Treatment with *Medscape Respiratory Care* 1998; 2(1).
Borowitz SM, Topical Corticosteroid Preparations *Pediatric Pharmacotherapy* 1996;2(1).
Poole MD Declining Antibiotic Effectiveness in Otitis Media A Convergence of Data. *Ear Nose & Throat Journal* 1998, 77(6);444–47.
Estrada B, Infectious Causes of Hearing Loss Beyond Otitis Media *Infect Med* 14 (3):239–244, 1997.
Osborne DW, Henke JJ, Skin Penetration Enhancers Cited in the Technical Literature *Pharmaceutical Technology* Nov. 1997, p58–86.
Modeland V. When Bells Are Ringing (But There Aren't Any Bells).*FDA Consumer* vol. 13, No. 3.
Hulshof JH, Vermen P, The Value of Tocanaide in the Treatment of Tinnitus, *Arch Otorhinolaryngol* 1985; 241 (3):279–83.
Pulec JL, Hodell SF, Anthony PF, Tinnitus: Diagnosis and Treatment *Ann Otol Rhinol Laryngol* 1978 Nov.–Dec.;87(6Pt1):821–33.
Von Wedel H, Von Wedel UC, Zonowka P, Tinnitus Diagnosis and Therapy in the Aged Acta Otolaryngol Suppl-(Stockl) 1990;476:195–201.
Shea JJ, Medical Treatment Of Tinnitus *Acta Otorhinolaryngol Belg* 1985; 39(3):613–9.
Crinnion CL, McCarr GM, Misoprostol for Tinnitus *Ann Pharmacother* 1995 Jul.–Aug.; 29(7):782–4.
Denk DM, et al, Caroverine In Tinnitus Treatment *Acta Otolaryngol* (Stock h) 1997 Nov.;117(6):825–30.
Petrus EJ et al Randomized, Double–Masked, Placebo–Controlled Clinical Study of the Effectiveness of Zinc Acetate Lozengos On Common Cold Symptoms in Allergy–Tested Subjects. *Current Therapeutic Research* 1998;59/9;595–607.
Bylander–Groth A, Stenstrom C, Eustachian Tube Function and OtitisMedia in Children. *Ear, Nose & Throat Journal* 1998;77(9);762–69.

*Primary Examiner*—Keith D. MacMillan

[57] ABSTRACT

A topical ear composition that uses penetration enhancers to diffuse the therapeutic agents through the tympanic membrane into the middle and inner ear for the purpose of reducing the inflammation of ear tissues, providing pain relief, and introducing agents with antimicrobial activity to combat infection. The composition reduces swelling of the lining membranes of the middle and inner ear, prevent the destructive effects of inflamation, inhibit the production of prostaglandins, reduce symptoms of tinnitus and vertigo, improve and prevent paralysis of the facial nerve, relieve labyrinthitis, and prevent hearing loss.

21 Claims, 2 Drawing Sheets

COMPOSITION TO TREAT EAR DISORDERS

FIELD OF THE INVENTION

A therapeutic composition for the relief and prevention of symptoms associated with ear disorders in humans and animals.

BACKGROUND OF THE INVENTION

Most ear disorders are the result of an inflammatory response to infections, allergic reactions, or trauma. The infection may be of bacterial, fungal or viral origin and determination of the precise etiology is not practical since the causative organism is often difficult to isolate and culture. The determination of a viral cause is even more difficult to establish. Trauma, as a cause of ear disorders is made on the basis of a medical history and radiological confirmation.

It is important to treat the inflammation as soon as possible to reduce the sequella of hearing loss, tinnitus, facial nerve palsy, mastoiditis, labyrinthitis, vertigo, and possible encephalitis. Otitis is a non-specific term that describes a symptom and indicates an inflammation of the ear. The ear is anatomically divided into the external, middle and inner ear.

The external ear consists of the auricle and the external canal, a tube like structure that ends at the tympanic membrane (eardrum). Otitis externa (swimmer's ear) is an inflammation of the external canal which occurs in hot, humid weather, after cooling off in the pool and by those who enjoy aerobic exercises. Normally, cerumen (ear wax) and the acid pH of the external auditory canal protect the ear from infection. The canal can become inflamed and infected when the epithelium lining the canal becomes injured, as can occur after attempts to remove cerumen or entrapped water from the ear canal. The epithelium becomes macerated and susceptible to infection. The epithelium of the external auditory canal is tightly attached to the underlying bone or cartilage, and even a little swelling produces a great deal of pain. The macerated epithelial cells form a red and scaly dermatitis that may encroach on the epithelium of the tympanic membrane. A cellulose tampon (Pope ear wick) is sometimes inserted into the auditory canal and moistened with antibiotics to control the infection and drying-medications or steroids to relieve the swelling. Fungal infections usually resolve when the acidic pH is restored. In diabetic or immunocompromised persons, otitis externa may progress to cellulitis of the scalp and osteomyelitis of the skull. Untreated or chronic otitis externa can cause an inflammation of the tympanic membrane and initiate an inflammation of the middle and inner ear.

The middle ear or tympanic cavity, is an air-filled cavity in the temporal bone that contains three small bones (malleus, incus and stapes) that transfer sound from the tympanic membrane to the oval window of the inner ear. The tympanic cavity resembles a red blood cell in appearance, since it is narrow and rounded, compressed at the center and enlarged peripherally. It is likened to a sump pit, 2 mm across the center, 15 mm in vertical diameter, 4 mm at the floor and 6 mm at the roof. The floor of the cavity overlies the jugular vein, the anterior wall is the internal carotid artery, the posterior wall contains the facial nerve, the tympanic membrane occupies the lateral wall and inner ear the middle wall. The eustachian tube connects the middle ear with the back of the nasopharynx. The tube's function is to allow air to enter the middle ear and maintain equal atmospheric pressure on both sides of the tympanic membrane. An inflammation of the lining of the eustachian tube, due to infection or allergies, causes the tube to close and either creates a vacuum or the accumulation of fluid in the middle ear resulting in otitis media.

Otitis media is a painful inflammation of the middle ear and ranks second only to the common cold as the most frequent illness among children in the United States. Acute otitis media is usually accompanied by fever, swelling, inflammation of the eardrum and considerable pain. Otitis media develops when bacteria or viruses, usually associated with colds or sore throats, make their way up the eustachian tube, from the upper part of the throat behind the nose to the middle ear. When fluid accumulates in the middle ear the condition is known as otitis media with effusion or "glue ear." This condition can lead to hearing loss and affect a child's learning and language skills.

Nearly 70 percent of U.S. children will develop otitis media by age 2. Otitis media is a frequent problem in children because the eustachian tube is shorter, wider, and more horizontal than in adults. Many children will outgrow their susceptibility to the infection by age 5. Over half of those who experience acute otitis media will have repeated episodes and the condition may become chronic. Otitis media is the most common cause of hearing loss in the U.S. and represents a significant disability interfering with childhood learning processes. Estrada B, *Infect Med* 1997; 14(3): 239–44. Otitis media accounts for over 35 percent of all visits to pediatricians each year and represents more than $3.5 billion in U.S. health care costs annually.

Otitis media, with or without effusion is the most common reason for prescribing antibiotics to children. The FDA found that about 14 percent of all courses of antibiotics prescribed in the United States were for otitis media. Seventy percent of ear infections have a bacterial etiology and 30 percent are viral in origin. Three types of bacteria, *Streptococcus pneumoniae, Hemophilus influenza* and *Moraxella catarrhalis* cause 50 to 90 percent of middle ear infections. Many of these bacteria are now resistant to antibiotics. Some children experience life threatening reactions to the antibiotics.

When medical management is not successful, plastic tubes are surgically inserted into the tympanic membrane to drain the middle ear. This surgical procedure known as tympanostomy, is the most common surgery performed on children under age 2. In 1988, 800,000 children received 1.3 million tympanostomy tubes. Of these, 30 percent were replacements. Risks of using ear tubes include: risks associated with general anesthesia; tympanosclerosis in 51 percent of patients; persistent otorrhea in 13 percent of patients and an average 5-db hearing loss. Thirty percent of children receiving one set of tubes will receive a second set within 5 years. A study published in JAMA, Apr. 27, 1994, found that 25 percent of tympanostomies were inappropriate, and in 30 percent the benefits did not outweigh the risks of general anesthesia. In 1986, 31 million visits to physicians were due to otitis media, and total direct and indirect costs for that year have been estimated at $3.5 billion. Surgical costs for procedures for otitis media exceed $1.2 billion annually.

The inner ear is concerned with the reception of sound and balance. The movement of the ear ossicles excite the perilymph fluid in the cochlea, which stimulate the nerve endings in the hair cells of the organ of Corti. The acoustic nerve then caries impulses to the brain for purposes of interpreting sound. The labyrinth is the collective name for the sense organs of equilibrium, consisting of the three semicircular canals and the utricle and saccule which connect with the cerebellum and the brainstem. Since the organs for hearing and balance are within the same compartment of the temporal bone, they are often affected by the same disorders. Inflammation in the middle ear frequently causes inflammation in the inner ear resulting in disorders of hearing and balance.

As far as the inventor is aware the prior art has not provided any topical composition which specifically directs therapeutic agents simultaneously to the external, middle, and inner ear, to treat and prevent the effects of inflammation and infection.

SUMMARY OF THE INVENTION

It is the object of the present invention to provide a topical composition, which is administered into the external ear canal by means of drops or the use of an impregnated porous media placed into the external ear canal to the tympanic membrane, whereby a penetration enhancer enables the active agents to provide pain relief and enter the middle ear and reduce inflammation and the symptoms associated with inflammation of the middle and inner ear, and introducing agents with antimicrobial activity to combat infection.

DETAILED DESCRIPTION OF THE INVENTION

Figure 1:
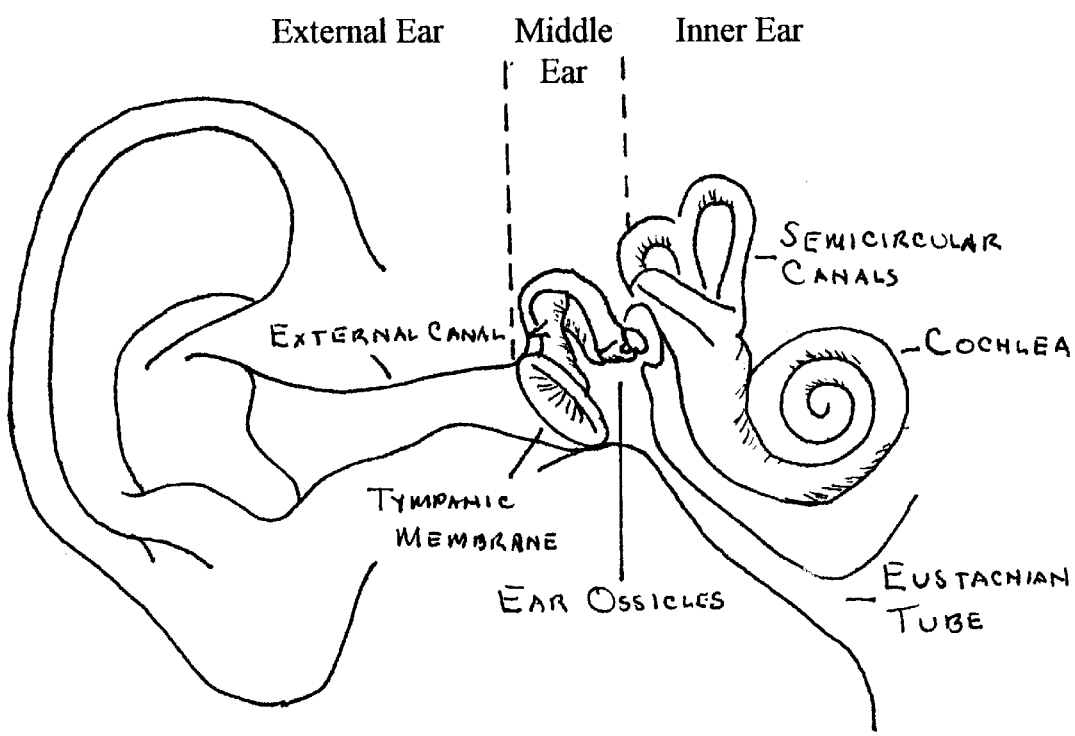
FIG. 1 is a cross section of the human ear showing the three anatomical divisions: external, middle and inner ear.
Figure 2:
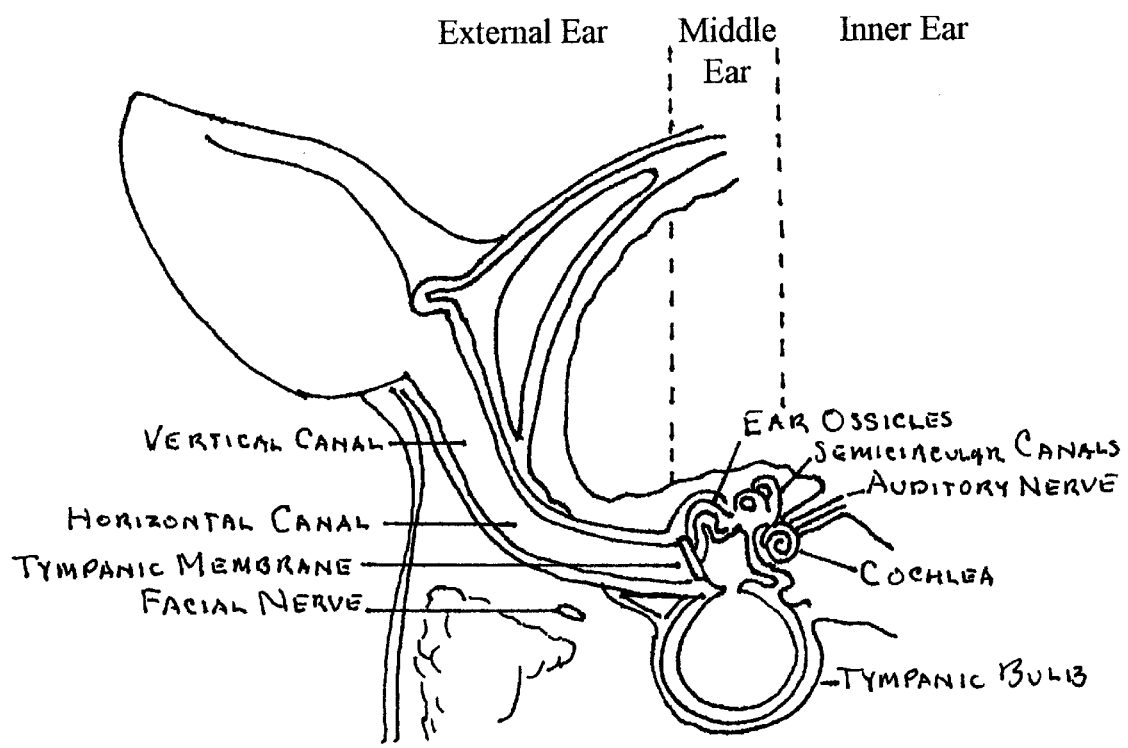
FIG. 2 is a cross section of a canine ear showing the two anatomical divisions of the external canal, middle and inner ear.

The external, middle and inner ear are so closely connected that an infection or inflammation of one anatomical division usually effects all three components. Most pathology originates in the middle ear. Pain is usually the presenting symptom as a result of tissue swelling of the lining of the middle ear and stretching of the tympanic membrane.

Treatment of middle ear disorders usually consists of an oral or intramuscular injection of antibiotics. Large doses of antibiotics are required due to metabolism in the liver and dilution in the bloodstream to deliver a small amount of the antibiotic to the ear tissues. Current ear drops have limited use for the external canal and tympanic membrane. The inventor is not aware of any ear drop composition that uses penetration enhancers to diffuse the therapeutic agents through the tympanic membrane into the middle and inner ear for the purpose of reducing the inflammation of ear tissues, providing pain relief, and introducing agents with antimicrobial activity to combat infection.

Penetration Enhancers

A penetration enhancer or permeation enhancer is an agent used to increase the permeability of the skin to a pharmacologically active agent to increase the rate at which the drug diffuses through the skin and enters the tissues and bloodstream. A chemical skin penetration enhancer increases skin permeability by reversibly damaging or by altering the physiochemical nature of the stratum corneum to reduce its diffusional resistance. In a review of the technical and patent literature up to 1996, more than 275 different chemical compounds were found to be cited as skin penetration enhancers. Most of the compounds are generally recognized as safe (GRAS) ingredients that would often be considered inert by a formulator. Osborne DW, Henke JJ, *Pharmaceutical Technology*, November 1997, pp 58–86. Examples of penetration enhancers include: alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof.

A number of patents disclose the use of penetration enhancers to deliver medications transdermally. Grasela et al, U.S. Pat. No. 5,837,289, discloses the use of at least two separate penetration enhancers in a cream to deliver an extensive list of medications. In U.S. Pat. No. 5,238,933 (Catz et al) disclose a skin permeation enhancer composition comprising a lower aliphatic ester of a lower aliphatic carboxyl acid in combination with a lower alkanol to administer an active agent. In U.S. Pat. No. 5,229,130 (Sharma et al) disclose a vegetable oil-based skin permeation enhancer to deliver active agents through the skin. Tsuk, U.S. Pat. No. 4,933,184, discloses a transdermal composition that uses methanol either sequentially or simultaneously to deliver drugs. None of the above cited patents teach or state any use for the treatment of ear disorders.

Anesthetics/Analgesics

Pain is usually the presenting symptom of external and middle ear inflammations. The pain response is a protective reflex system warning an individual of tissue injury. Topical anesthetics can be mixed with the penetration enhancers to relieve the pain associated with ear disorders.

Local anesthetics produce a reversible block to conduction along the nerve fiber. The anesthetic must first penetrate the lipid-rich myelin sheath of the nerve. The duration of the anesthetic depends on how well the anesthetic binds to the nerve membrane protein. Two major classes of local anesthetics used in the nonprescription treatment of pain are esters and amides. Examples of those in the ester class include benzocaine, butamben picrate and tetracaine. Examples of those in the amide class are dibucaine, prilocaine, etidocaine, mepivacaine, bupivicaine and lidocaine. Other examples are proprionic acid derivatives, fenamates, pyrrolealkanoic acids, pyrazolone derivatives, oxicams, pramoxine, and others and mixtures thereof Nayak in U.S. Pat. No. 5,447,930, discloses the use of the topical anesthetic, pramoxine, with a cellulose carrier to treat pain and irritation of the skin from insect bites, burns and allergic reactions.

Lidocaine is an active surface anesthetic. It has a short latency period, long duration of action and low toxicity. As a local anesthetic it relieves pain and itching associated with inflammation of the external and middle ear. By topically applying lidocaine to the skin, the first-pass effect in the liver, where lidocaine is metabolized, is avoided and the bioavailability is increased. Lidocaine has also been shown to have broad-spectrum effect against both gram-negative and gram-positive organisms. Aldous WK, *Ear, Nose & Throat Journal* 1998;77(7):554–57. U.S. Pat. No. 5,827,529, (Ono et al) discloses the use of lidocaine in an adhesive gel base to slowly release the lidocaine to treat herpes zoster neuralgia and postherpetic neuralgia. Watson, U.S. Pat. No. 4,851,442, discloses the use of lidocaine, dimethyl sulfoxide and citric acid to treat arthritis. In U.S. Pat. Nos. 4,628,063, and 4,914,131 (Haines et al) disclose the topical administration of lidocaine, as an antivaral agent, and pentothenol to treat herpes simplex infections.

In the 1930s, a physician injected procaine, a nerve-blocking anesthetic into a surgical patient's nose. The patient also had tinnitus and remarked that the tinnitus cleared temporarily after the injection. Researchers estimate that 36 million Americans have tinnitus, of which 7.2 million sought medical help. *FDA Consumer,* April 1989; Vol 23, No 3. In a double-blind controlled trial, lidocaine was reported to suppress tinnitus in 81% of the patients treated. Hulshof JH, Vermeij P. *Arch Otorhinolaryngol* 1985;241(3):279–83. In treating tinnitus, lidocaine is usually administered by injection.

Tinnitus is described as a ringing sensation or other head noised that are perceived in the absence of any external noise source. Tinnitus has been reported in as high as 80% of patients seen in an otolaryngology practice. This symptom is particularly marked in patients with a hearing loss and can be so severe that it becomes disabling. Pulec JL, Hodell SF, Anthony PF. *Ann Otol Rhinol Laryngol* 1978 November–December;87(6 Pt 1):821–33. The main cause of tinnitus is exposure to excessively loud noise, which can be found at rock concerts, movie theaters, nightclubs, construction sites, guns, power tools, and stereo headphones. One study found that younger patients suffer more from tinnitus than older subjects. Von Wedel H, et al. *Acta Otolaryngol Suppl* (*Stockh*) 1990;476:195–201. In U.S. Pat. Nos. 4,956, 391 and 5,064,858, Sapse discloses the use of procaine with a complexing agent to treat tinnitus, narcotics addiction and Alzheimer's disease.

Tinnitus occurs in 60% of inner ear diseases and is caused by an altered discharge in the auditory pathway between the inner hair cells of the cochlea and the afferent dendrites of the auditory nerve. Lidocaine, and its analogues, act by blocking part of the transmission through each nerve synapse, having more effect on the slow multisynaptic pathway through the reticular formation than the rapid pathway to have more effect on the low frequency slow pathway tinnitus than the rapid pathway high frequency tinnitus. Shea JJ. *Acta Otorhinolaryntol Belg* 1985;39(3) :613–9. Studies using lidocaine, nortryptyline, or alprazolam have shown encouraging results. Crinnion, McCart GM, *Ann Pharmacother* 1995 July–August;29(7–8):782–4. Caroverine, a quinoxaline derivative, has also reduced the symptom of tinnitus. Denk DM et al, *Acta Otolaryngol* (*Stockh*) 1997 November;117(6):825–30. In U.S. Pat. No. 4,954,486, Guth disclosed the use of furosemide to treat tinnitus.

It is the object of this invention to incorporate an anesthetic, such as lidocaine, with a penetration enhancer to relieve the pain in the external and middle ear, treat infection, and reduce tinnitus and in the inner ear.

Zinc Salts

Zinc salts have anti-inflammatory and anti-infective properties. In a recent published article, Petrus EJ et al., *Current Therapeutic Research,* 1998; 59/9: 595–607, the inventor served as chief investigator for a randomized, double-masked, placebo-controlled clinical study of the effectiveness of zinc acetate lozenges on common cold symptoms in allergy-tested subjects. Those subjects who used the zinc lozenges had both a shorter duration and severity of common cold symptoms. Those subjects who were positive for allergies, were more responsive to zinc by having a shorter duration of nasal symptoms. The study cited many references that reported the following benefits and effects of zinc salts:

Zinc is an essential trace element in human biology that is known to be necessary for many biologic functions, such as growth, appetite, testicular maturation, skin integrity, mental activity, wound healing, and immune system maintenance. Approximately 300 enzymes are known to require zinc for their activities. Zinc deficiency in humans is widespread and is more prevalent in areas where the population subsists on cereal proteins. Clinical manifestations of zinc deficiency include: growth retardation, hypogonadism in males, neurosensory disorders, cell-mediated immunological dysfunctions, increased maternal morbidity, premature delivery, and adversely affects the proliferation, regulation and maturity of lymphocytes.

Most colds are caused by rhinoviruses. Zinc ions inhibit rhinoviral replication and the cleavage of rhinovirus polypeptides. Rhinoviruses have been found to bind with a receptor named ICAM-1 found on nasal epithelium. It has been proposed that zinc ions complex with ICAM-1 binding sites and prevent the rhinovirus from attaching to the nasal tissue. If zinc-blocked viruses do not infect nasal tissue cells to replicate, then the infectious process would be interrupted and the cold duration markedly shortened. Zinc is also believed to act as a protease inhibitor in its effect against rhinovirus infections. Other common cold-causing viruses inhibited by zinc ions include herpes simplex viruses and coxsackie viruses.

Zinc ions have other benefits that may shorten the severity and duration of non-viral symptoms associated with the common cold. Zinc has antibacterial activity. It can inhibit the growth of Streptococci and Actinomyces when used as a dentifrice. Zinc compounds have antiseptic, antifungal and astringent properties. As an astringent, zinc can be used therapeutically to arrest hemorrhage by coagulating blood, check diarrhea, reduce inflammation of mucus membranes, promote healing, toughen skin, and decrease sweating. Zinc's dominant biological action is membrane stabilization.

Zinc has been shown to be an essential element for the function of the immune system. Regarding the effect of zinc on allergies, it is known that mast cells have been implicated as mediators of Type I allergic reactions and common cold symptoms by causing tissue redness, inflammation, nasal congestion, release of mucus from goblet cells, nose and throat pain, tickling and itchiness, and indirectly, coughing and sneezing. Mast cell derived reactions result from the release of histamine, heparin, prostaglandins, SRS-A, and various vasoactive amines from granules on the surface of mast cells, possibly including kinins. One product of mast cell-induced inflammation in response to rhinoviral infection is fever. The inhibitory effect of zinc on histamine release from mast cells are attributed to its action on the stabilization of the mast cell membrane. Zinc ions were found to stabilize cell plasma membranes and prevent induced histamine and vasoactive amine release from tissue mast cells. It has been observed that unsequestered zinc ions (4 to 20 millimolar) are released in inflammation from mast cell granules suggesting a common linkage between allergy and common colds. Zinc is a competitive antagonist of the calcium-dependent IgE and f-met peptide mediated histamine release from human basophils and suggested that zinc compounds might be considered for the treatment of allergic disorders.

Otitis media is believed due in part to both inflammation of the middle ear mucosa and eustachian tube dysfunction.

The mucosal edema is produced by inflammatory mediators. Bylander-Froth A, Stenstrom C, *Ear, Nose & Throat Journal* 1998;77(9):762–69. Zinc reduces the level of allergic inflammatory mediators. Zinc has an inhibitory effect on the release of histamine from mast cells due to its stabilizing effect of the mast cell membrane.

The inner ear has the highest concentration of zinc in the body. Studies have suggested that a zinc deficiency can cause a hearing-nerve impairment and tinnitus. Shambaugh GE. *Am J Otol* 1989 March;10(2):156–60. Sixteen percent of adults have clinically relevant hearing impairment, defined as a loss of sound perception of 25 dB or more, making hearing impairment a major public health concern. The inner ear converts the sound's vibrations to fluid movements that stimulate hair cells in the organ of Corti that are transmitted by the auditory nerve to the brain. A difficulty in the recirculation of potassium ions in the organ of Corti may be responsible for hearing loss. Stell KP, *Lancet* 1998;339: 1545–47. Excessive noise can result in direct shearing of the hair cells and the release of chemicals, such as glutamate and nitric oxide. Kenurenate, a glutamate antagonist prevents dendtiric damage. Nitric oxide, a mediator of hair cell damage in the cochlea can be blocked by an inhibitor of nitric oxide. Prasher D, *Lancet,* Oct. 17, 1998 p1240(1). Zinc has been noted to be a very potent inhibitor of nitric oxide synthase, the enzyme responsible for the production of nitric oxide. Cuajungco MP, Lees GJ, *Neurobiol Dis* 1997;4 (3–4):137–69.

Zinc compounds are acknowledged as astringents and beneficial in wound healing, reducing inflammation, and has antimicrobial, antifungal and antiviral activity. Zinc is the active agent in formulations to treat diaper rash, decubitus ulcers, and abrasions. Zinc stabilizes the cell membranes and inhibits the formation of free radicals. Zinc also strengthens the integrity of blood vessel walls by reducing the membrane permeability and stopping bleeding.

Ear infections in dogs respond to the same treatment used in humans. Due to the amount of cerumen found in dogs ears a cerumenolytic may be incorporated into the formulation. Thomas DW, *DOGworld* November 1996; 38–9. In U.S. Pat. No. 4,025,620 (Beyer et al) disclose the use of diethylanolamine fusidate, nystatin, neomycin B sulfate, prednisone and vegetable oil.

Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

It is a further object of this invention to incorporate a zinc salt, such as zinc sulfate, with an anesthetic, such as lidocaine, and a penetration enhancer, such as glycerol to relieve the pain in the external and middle ear, reduce the inflammation and obstruction of the eustachian tube, and treat the tinnitus and hearing loss associated with disorders in the inner ear.

Anti-Inflammatory Agents

In formulating the therapeutic composition, more potent anti-inflammatory agents may be required. Corticosteroids inhibit expression of mRNA for interleukin 1 (IL-1) and tumor necrosis factor (TNF), production of phospholipid derivatives such as platelet-activating factor (PAF) and prostaglandins, activity of inducible nitric oxide synthase, and complement activation. In cases where bacterial meningitis is involved the incidence of long-term hearing loss and other neurological sequelae are reduced. Townsend GC, Scheld WM. *Infect Med* 1995 12(12):701–10. Two percent of patients with chronic rhinitis develop nasal polyps, an outgrowth of the nasal mucosa. The polyps may cause obstruction and edema of the eustachian tube. Mast cells accumulate in the nasal epithelium and release histamine that produces allergic symptoms. Topical corticosteroids reduce polyp size, reduce edema and intercellular fluid, increase airway patency, decrease albumin, IgG and IgE in nasal secretions. Winder JA. *Medscape Respiratory Care* 1998 2(1). Topical corticosteroid preparations are rated as low potency, such as hydrocortisone, moderate potency, such as fluticasone proprionate, high potency, such as betamethasone, and very high potency, such as halobetasol propionate. Borowitz SM. *Pediatric Pharmacotherapy* 1996; 2(1). Examples of topical corticosteroids include, but are not limited to: hydrocortisone, prednisone, fluprednisolone, triamcinolone, dexamethasone, betamethasone, methylprednisolone, fluocinolone acetonide, flurandrenolone acetonide, and fluorometholone.

Nonsteroidal anti-inflammatory agents (NSAIDs) are also useful in relieving pain and tissue swelling, chiefly by inhibiting the biosynthesis of prostaglandins. NSAIDs fall in seven major classes: proprionic acid derivatives, indole derivatives, fenamates, pyrrolealkanoic acids, pyrazolone derivatives, oxicams and salicylic acids.

It is a further object of this invention to incorporate anti-inflammatory agents, such as hydrocortisone with an anesthetic, such as lidocaine, and a penetration enhancer, such as glycerol to relieve the pain in the external and middle ear, reduce the inflammation and obstruction of the eustachian tube, and treat tinnitus and hearing loss associated with disorders in the inner ear.

Anti-Infective Agents

Since the introduction of antibiotics, they have been successfully used to treat infections associated with otitis. Besides antibiotic resistance in otitis media, achieving a serum level above the minimum inhibitory concentration (MIC) has been reported. Poole MD. *Ear, Nose & Throat Journal* 1998; 77(6):444–47. Because of dilution by the bloodstream and metabolism by the liver, effective antimicrobial levels to the ear may not be reached, leading to the erroneous conclusion that the microbe is resistant to the antibiotic or that the antibiotic is not effective. Direct application to the ear by means of drops may overcome this limitation. In U.S. Pat. No. 5,061,729 (Kineses et al) discloses an ear drop containing a sulfhydryl compound, antibacterial agent, anti-inflammatory agent and stabilizers.

Examples of anti-infective agents include: penicillins; cephalosporins; erythromycins; azalides; tetracyclines; quinolones; fluoroquinolones; sulfonamides; chloramphenicol; aminoglycosides; bacitracin; mupirocin; lincomycin; clindamycin; vancomycin; antifungal drugs; antiviral chemotherapy such as acyclovir, gancyclovir; interferons; mono and polyclonal antibodies; thimerasol; and admixtures thereof. In U.S. Pat. No. 5,843,930 (Purwar et al) discloses an ear drop containing ciproflaxacin, a viscosity augmenter, hydrocortisone, preservative, and dispersant, but requires a perforated tympanic membrane for the composition to enter the middle ear.

It is a further object of this invention to incorporate anti-infective agents, such as an antibiotic with an anesthetic, such as lidocaine, and a penetration enhancer, such as glycerol to relieve the pain in the external and middle ear, reduce the inflammation and obstruction of the eustachian tube, and treat tinnitus and hearing loss associated with disorders in the inner ear.

The therapeutic composition further comprises additional active agents selected from a group consisting of anti-inflammatory agents, anti-infectives, anti-fungal and anti-viral medications; vasodilators, magnesium salts, calcium salts, mucolytics, antioxidants, preservatives, stabilizers, surfactants, aloe vera, carbonic anhydrase inhibitors, kynurenate, R-phenylisopropyladenosine (R-PIA), and others.

Antioxidants enhance the healing of infected and noninfected wounds by reducing the damage caused by oxygen radicals. Injured external ear tissues undergo free radical reactions more quickly than do healthy ones. It has been suggested that free radicals play a role in collagen destruction. Antioxidants are the main host defense produced in response to the production of free radicals. Free radicals are produced in the hair cells after metabolic overload from intense sound exposure and converted to highly destructive hydroxyl radicals in the stria vascularis of the organ of Corti. Antioxidants such as allopurinal, lazaroids, a-D-tocopherol and mannitol have helped reduce the threshold shift after noise exposure. Drugs, such as R-PIA, that boosts antioxidant activity can mitigate against noise-induced damage to inner hair cells.

Antioxidant defense mechanisms include but are not limited to: vitamin E, pyruvate B-carotene, selenium, N-acetylcysteine, vitamin C, antioxyenzymes such as superoxide dismutase (SOD), catalase, glutathione peroxidase, and glutathione reductase together with the enzymes of the pentose monophosphate shunt pathway that regenerate NADPH, allopurinal, lazaroids, and mannitol. Pyruvate is one of the few antioxidants that readily enter cells, making it an ideal cytoplasmic antioxidant. Pyruvate alone or in combination with alpha tocopherol, vitamin E, inhibits reactive oxygen-induced damage. Vitamin E, a term that encompasses a small group of related tocopherols, is the major lipid-soluble antioxidant responsible for protecting the polyunsaturated fatty acids in membranes against lipid peroxidation. Tocopherols protect lipids by scavenging peroxyl radicals precluding further chain propagating steps. One or more antioxidants could be formulated in the composition.

The therapeutic topical composition can be formulated into many different configurations. One example is a formulation of a penetration enhancer, such as glycerol, an anesthetic, such as lidocaine, and a zinc salt such as zinc sulfate. The formulation could also be a combination of two or more penetration enhancers, such as glycerol and lecithin, anesthetics, such as lidocaine and benzocaine and zinc salts, such as zinc sulfate and zinc acetate mixed to provide the maximum therapeutic effect, yet useful in the nonprescription market. Some formulations of penetration enhancers, anesthetics, anti-inflammatory agents and anti-infectives could be prescription items. While zinc salts demonstrate, antibacterial, anti-fungal, anti-viral, and anti-inflammatory activity, it may be desired to use corticosteroids and antibiotics. Examples would include a composition of dimethylsulfoxide, lidocaine, triamcinolone, and clarithromycin.

The above-mentioned patents are hereby incorporated by reference.

Although illustrative embodiments of the invention have been shown and described, a wide range of modifications, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A therapeutic composition useful for the prevention and relief of symptoms associated with ear disorders in humans and animals comprising:
   a) penetration enhancers, and
   b) anesthetics, and
   c) zinc salts, 1.0 to 10% by weight relative to the total composition,
whereby, the penetration enhancer allows the analgesics and zinc salts to penetrate the tympanic membrane and affect the middle and inner ear.

2. The therapeutic composition of claim 1, wherein said penetration enhancers are selected from groups consisting of: alcohols, polyols, sulfoxides, esters, ketones, amides, oleates, surfactants, alkanoic acids, lactam compounds, alkanols, and admixtures thereof.

3. The therapeutic composition of claim 1, wherein said anesthetics and/or analgesics are selected from: amino-amides, nonsteroidal anti-inflammatory agents (NSAIDs), and admixtures thereof.

4. The therapeutic composition of claim 1, wherein said zinc salt is selected from the group consisting of: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, zinc glycinate, and admixtures thereof.

5. The therapeutic composition of claim 1, further comprising additional active agents selected from the group consisting of: anti-inflammatory agents; anti-infectives; vasodilators, magnesium salts, calcium salts, mucolytics, antioxidants, aloe vera, carbonic anhydrase inhibitors, kynurenate, R-phenylisopropyladenosine (R-PIA).

6. The therapeutic composition of claim 1, further comprising a carrier that allows administration by drops or by means of an impregnated porous media placed into the external ear canal to the tympanic membrane.

7. The therapeutic composition of claim 2, wherein said penetration enhancer is glyerol and represents 85 to 90% by weight relative to the total composition.

8. The therapeutic composition of claim 3, wherein said anesthetic is lidocaine and represents 1.0 to 5.0% by weight relative to the total composition.

9. A therapeutic composition useful for the prevention and relief of symptoms associated with ear disorders in humans and animals comprising:
   a) penetration enhancers, and
   b) anesthetics and/or analgesics, 1.0 to 6.0% by weight relative to the total composition, and
   c) anti-inflammatory agents, and
   d) anti-infective agents,
whereby, the penetration enhancer allows the anesthetics, anti-inflammatory and anti-infective agents to penetrate the tympanic membrane and affect the middle and inner ear.

10. The therapeutic composition of claim 9, wherein said penetration enhancers are selected from the group consisting of: alcohols, polyols, sulfoxides, esters, ketones, amides, oleates, surfactants, alkanoic acids, lactam compounds, alkanols, and admixtures thereof.

11. The therapeutic composition of claim 9, wherein said anesthetic and or analgesic is selected from the group consisting of: amino-amides, nonsteroidal anti-inflammatory agents (NSAIDs) and admixtures thereof.

12. The therapeutic composition of claim 9, wherein said anti-inflammatory agents are selected from the group consisting of: corticosteroids, cyclophosphamide; zinc salts, and admixtures thereof.

13. The therapeutic composition of claim 9, wherein said anti-infective is selected from the group consisting of: penicillins; cephalosporins; erythromycins; azalides; tetracyclines; quinolones; fluoroquinolones; sulfonamides; chloramphenicol; aminoglycosides; bacitracin; mupirocin; lincomycin; clindamycin; vancomycin; antifungal drugs; antiviral chemotherapy; mono and polyclonal antibodies; thimerasol, zinc salts, and admixtures thereof.

14. The therapeutic composition of claim 9, further comprises additional active agents selected from a group comprising: vasodilators, magnesium salts, calcium salts, mucolytics, antioxidants, aloe vera, carbonic anhydrase inhibitors, kynurenate, R-phenylisopropyladenosine (R-PIA).

15. The therapeutic composition of claim 9, further comprising a carrier that allows administration by drops or by means of an impregnated porous media placed into the external ear canal to the tympanic membrane.

16. The therapeutic composition of claim 11, wherein said penetration enhancer is glycerol and represents 30 to 80% by weight relative to the total composition.

17. The therapeutic composition of claim 12, wherein said anti-inflammatory agent is triamcinolone and represents 0.1 to 3.0% by weight relative to the total composition.

18. The therapeutic composition of claim 13, wherein said anti-infective agent is clarithromycin and represents 0.1 to 4.0% by weight relative to the total composition.

19. The therapeutic composition of claim 1, wherein said penetration enhancers are selected from groups comprising: ionic compounds, dimethyl sulfoxides, azones, solvents, fatty alcohols, fatty acid esters, fatty acids, fatty alcohol ethers, enzymes, amides, volatile oils, herbal extracts, N-methyl pyrrolidone and admixtures thereof.

20. A method for the prevention and relief of symptoms associated with ear disorders in humans and animals by use of a composition comprising:
    a) penetration enhancers, and
    b) anesthetics and/or analgesics, and
    c) zinc salts,
whereby, the penetration enhancer allows the anesthetics and/or analgesics and zinc salts to penetrate the tympanic membrane and affect the middle and inner ear, wherein said ear disorders are associated with pain, swelling of lining membranes of the middle ear, infection, inflammation, tinnitus, vertigo, paralysis of the facial nerve, labyrinthitis, and hearing loss.

21. A method for the prevention and relief of symptoms associated with ear disorders in humans and animals comprising:
    a) penetration enhancers, and
    b) anesthetics and/or analgesics, and
    c) anti-inflammatory agents, and
    d) anti-infective agents,
whereby, the penetration enhancer allows the anesthetics, anti-inflammatory and anti-infective agents to penetrate the tympanic membrane and affect the middle and inner ear, wherein said ear disorders are associated with pain, swelling of lining membranes of the middle ear, infection, inflammation, tinnitus, vertigo, paralysis of the facial nerve, labyrinthitis, and hearing loss.

* * * * *